(12) United States Patent
Højlund Nielsen et al.

(10) Patent No.: US 10,150,715 B2
(45) Date of Patent: Dec. 11, 2018

(54) DEHYDROGENATION OF ALKANES TO ALKENES

(71) Applicant: Haldor Topsøe, Kgs. Lyngby (DE)

(72) Inventors: Poul Erik Højlund Nielsen, Fredensborg (DK); John Bøgild Hansen, Humlebæk (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 15/507,985

(22) PCT Filed: Sep. 23, 2015

(86) PCT No.: PCT/EP2015/071858
§ 371 (c)(1),
(2) Date: Mar. 1, 2017

(87) PCT Pub. No.: WO2016/050583
PCT Pub. Date: Apr. 7, 2016

(65) Prior Publication Data
US 2017/0247302 A1     Aug. 31, 2017

(30) Foreign Application Priority Data

Sep. 29, 2014 (DK) ................................ 2014 00553

(51) Int. Cl.
*C07C 5/32*     (2006.01)
*C07C 5/327*    (2006.01)
*C07C 5/333*    (2006.01)
*C07C 5/46*     (2006.01)

(52) U.S. Cl.
CPC .............. *C07C 5/3332* (2013.01); *C07C 5/46* (2013.01); *C07C 2521/02* (2013.01); *C07C 2521/10* (2013.01); *C07C 2527/043* (2013.01); *C07C 2527/047* (2013.01); *C07C 2527/049* (2013.01); *C07C 2527/051* (2013.01)

(58) Field of Classification Search
CPC ............ C07C 5/3332; C07C 2527/051; C07C 2521/10
See application file for complete search history.

(56) References Cited

U.S. PATENT DOCUMENTS

| | | | |
|---|---|---|---|
| 2,315,107 A * | 3/1943 | Chickinoff | .............. C07C 5/321 585/661 |
| 3,787,517 A | 1/1974 | Haag et al. | |
| 3,801,661 A | 4/1974 | Hart et al. | |
| 4,420,649 A | 12/1983 | Antos | |
| 5,527,979 A * | 6/1996 | Agaskar | ................ C07C 5/3337 585/654 |
| 2004/0092784 A1 | 5/2004 | Legendre | |

(Continued)

FOREIGN PATENT DOCUMENTS

WO     WO 01/70655 A1     9/2001

OTHER PUBLICATIONS

Gibson et al. (The reaction between hydrogen sulfide and spherical pellets of zinc oxide, Ind. Eng. Chem. Process Des. Dev., 1980, 19, 231-237) (Year: 1980).*

(Continued)

*Primary Examiner* — Youngsul Jeong
(74) *Attorney, Agent, or Firm* — Blank Rome LLP

(57) ABSTRACT

Process for dehydrogenation of alkanesor alkylbenzenes by using metal sulfide catalyst under the presence of small amounts of hydrogen sulfide.

10 Claims, 5 Drawing Sheets

(56) References Cited

U.S. PATENT DOCUMENTS

Figure 1:
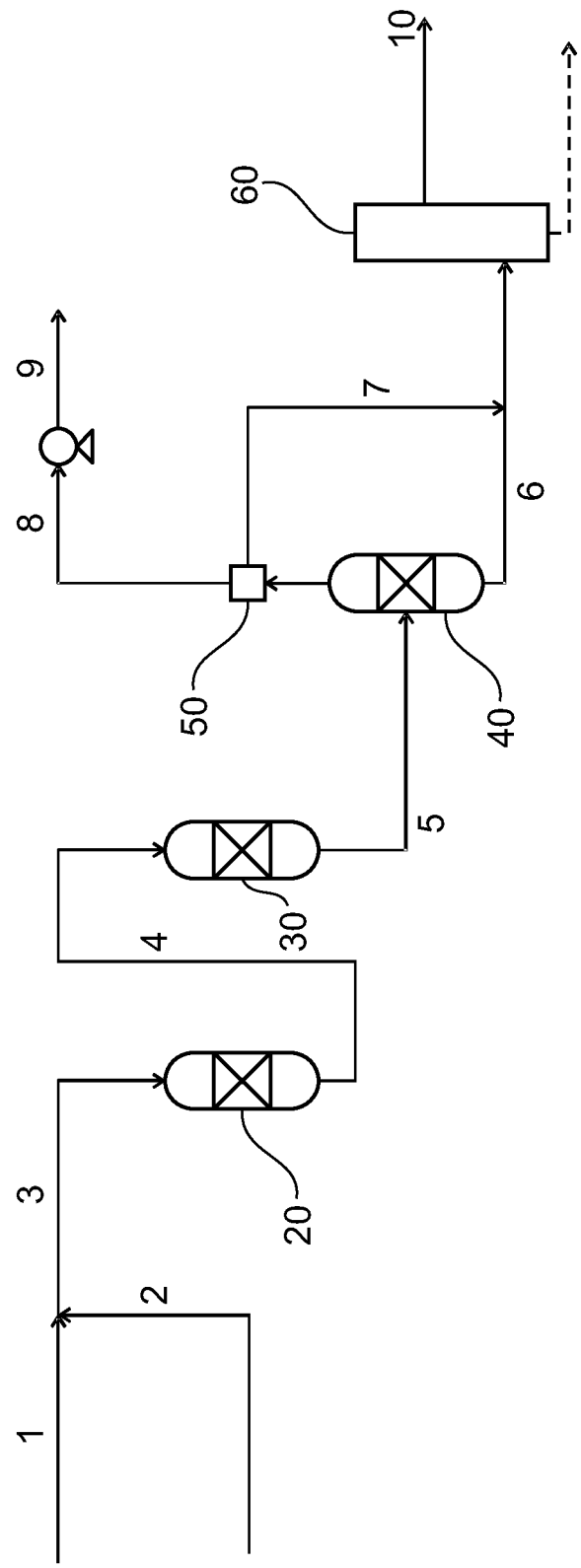

2006/0106268 A1* 5/2006 Kowaleski ............. B01J 23/745
585/444
2014/0114107 A1 4/2014 Gami
2015/0018593 A1 1/2015 Trischler

OTHER PUBLICATIONS

Saleh et al. (Interaction of hydrogen sulphide with nickel, tungsten and silver films, Transactions of the Faraday Society, 57 (1961): 1771-1780) (Year: 1961).*

* cited by examiner

DEHYDROGENATION OF ALKANES TO ALKENES

The present invention relates to a process for the dehydrogenation of alkanes to alkenes, primarily the dehydrogenation of ethane, propane and butane to the respective alkene products (olefins) ethylene, propylene and butylene. The present invention relates also to the dehydrogenation of alkenes to the corresponding unsaturated chemical compound. The present invention relates in particular also to the dehydrogenation of alkylbenzene to the corresponding unsaturated chemical compounds, primarily the dehydrogenation of ethylbenzene to styrene. More particularly, the dehydrogenation is conducted catalytically by contacting the alkanes, alkenes or alkylbenzene with a metallic sulfide (MeS) under the presence of hydrogen sulfide ($H_2S$) yet where no hydrogen sulfide ($H_2S$) is formed and without using steam as carrier gas in the process. Instead of steam as carrier gas, carrier gases having higher heat capacity to heat of evaporation ratio and which are produced in the process are or may be utilized.

Current state of the art in industrial processes for dehydrogenation of alkanes are high temperature processes typically operating above 500° C. and in all cases also low pressure processes amounting from the fact that dehydrogenation reaction $AH_2=A+H_2$ is endothermic requiring about 120 kJ/mole and involves forming more product moles than reactants. Thus both a temperature increase and low pressure lead to higher conversion. A is an unsaturated compound and as such highly reactive. The dehydrogenation of alkanes is normally carried out without diluents or with hydrogen as diluent. For dehydrogenation of ethylbenzene for production of styrene, current state of the art industrial processes are conducted by using a promoted iron oxide catalyst and with water/steam as carrier gas (diluent) and carbon suppressor.

One of the parasitic reactions in dehydrogenation is carbon formation, which leads to rapid deactivation of the catalyst. Thus, frequent regenerations of the catalyst may be necessary in certain applications. Carbon formation is not only a problem for the catalyst. Also the material used for the dehydrogenation reactor and for the piping has to be carefully selected, typically by using highly expensive alloys in order to avoid carbon attack resulting in the catastrophic form of corrosion known as metal dusting.

The use of metal sulfides for dehydrogenation of alkanes is known in the art. It is for instance known to use sulfided metal catalysts supported on silica in which the metal is Zn, Cu or Mn, Mo, Fe, Co, Ni for isobutane dehydrogenation. However, the metal sulfides present low stability since an otherwise high catalytic activity tends normally to drop quickly during the dehydrogenation.

U.S. Pat. No. 3,787,517 discloses oxidative dehydrogenation of paraffins, in which the paraffin (alkane) reacts with carbonyl sulfide (COS) as oxidant and in the presence of a supported heavy metal catalyst, such as iron on silica. The conversion of ethylbenzene to styrene according to this process is also disclosed.

Patent application US 2004/0092784 discloses a process for the catalytic conversion of alkanes to alkenes by reaction of the alkane with a sulfur containing compound in the presence of a metallic sulfide catalyst, but under the production of hydrogen sulfide in the process, i.e. by forming hydrogen sulfide as reaction product.

U.S. Pat. No. 3,787,517 discloses the use of mixed basic metal oxide/sulfide catalyst for the production of styrene from toluene by oxidative coupling of methane, does avoiding the use of ethylbenzene as feed and the use of superheated steam, which is normal in industrial production of styrene.

U.S. Pat. No. 3,801,661 discloses the dehydrogenation of non-aromatic alkanes to alkenes via metal sulfide catalysts in which $H_2S$ and steam are present, although not as co-reactants.

U.S. Pat. No. 4,420,649 discloses the dehydrogenation of dehydrogenatable hydrocarbons by using a pyrolyzed ruthenium carbonyl component, a rhenium component and a platinum group component. The catalyst is thus expensive and additionally there is no use of hydrogen sulfide ($H_2S$) in the dehydrogenation.

Patent application US 2015/0018593 discloses catalysts for the conversion of C2-C4 alkanes to olefins, in which the catalysts are metal carbide, metal nitride, metal silicide, metal phosphide, metal sulfide, or mixtures of these, combined with a non-Brønsted-acidic binder selected from $AlPO_4$, bentonite, AlN and $N_4Si_3$. There is no use of hydrogen sulfide ($H_2S$) in the dehydrogenation.

Patent application US 2014/0114107 discloses a variation of a conventional process for the dehydrogenation of ethylbenzene under the presence of steam, where benzene and toluene are recycled. There is no use of hydrogen sulfide ($H_2S$) in the dehydrogenation.

Metallic sulfide catalysts are well known for refinery processes like hydrotreating and so-called sour shift water gas shift processes. Yet, these processes typically take place at about 300° C. region whereas dehydrogenation takes place at temperatures around 600° C. Thus much more severe demands are set for the stability of such catalysts, notably thermal stability of the support as well as stability of the sulfide catalyst.

The prior art is thus replete with citations in which alkanes or ethylbenzene are dehydrogenated with metal sulfide catalysts in the presence of: sulfur containing compounds in the form of COS or sulfur containing compounds that yield hydrogen sulfide during the dehydrogenation process, or that yield $SO_2$ during the dehydrogenation process, or where the dehydrogenation is conducted in the presence of hydrogen sulfide and steam.

The use of steam in the dehydrogenation process, even though it does not act as reactant in the dehydrogenation is undesired, as steam requires to be produced by energy intensive evaporation and has to be condensed out again in the process. The heat of evaporation cannot be fully recuperated. For instance, in current processes for conversion of ethylbenzene to styrene, a large amount of steam is added to the ethylbenzene in order to suppress carbon formation on the catalyst, dilute the gas thus lowering the ethylbenzene partial pressure to favor the equilibrium and finally provide the heat of reaction by acting as a heat carrier.

It is therefore an object of the present invention to provide an alternative process for dehydrogenation of alkanes, alkenes or alkylbenzenes to the corresponding unsaturated chemical products which is able to maintain a high stability of the catalyst.

It is another object of the present invention to provide an alternative process for dehydrogenation of alkanes, alkanes or alkylbenzenes to the corresponding unsaturated chemical products which is simpler and more energy efficient and which at the same time enables maintaining high stability of the catalyst.

It is another object of the present invention to provide a process for dehydrogenation of alkanes, alkenes or alkylbenzenes which is more inexpensive than prior art processes.

These and other objects are solved by the present invention.

We have surprisingly found that metallic sulfided catalysts (sulfur passivated catalysts) can dehydrogenate alkanes or alkylbenzenes to respectively alkenes, such as propane to propene, and ethylbenzene to styrene, in an efficient manner, with a high stability and selectivity when the dehydrogenation reaction is conducted in the presence of small amounts of $H_2S$ yet without the use of steam as carrier gas. In particular, no sulfur containing compound in the form of COS, or $SO_2$ or elemental sulfur is needed as reactant in the dehydrogenation process. Accordingly, no $H_2S$ is formed as a result of the dehydrogenation process.

It turns out that the stability of the metallic sulfide catalyst is a function of the $H_2S/H_2$ molar ratio. Since we deal with the possible reactions $MeS+H_2=Me+H_2S$, with Me typically being Fe, Co, Ni, Mo, W, all are potential carbon forming agents in hydrocarbon streams whereas their sulfides and mixtures of these are hydrogenation/dehydrogenation catalysts.

A key element in existing dehydrogenation processes and which the present invention addresses is the heat transfer to the reaction. Particularly, in a conventional styrene process this is done by using steam as carrier gas. The reaction is often carried out by means of 2-3 adiabatic catalytic beds with reheating to 600-650° C. in between.

The sulfide based dehydrogenation process according to the present invention offers other significant advantages. Apart from avoiding unnecessary formation of $CO_2$ by steam reforming, since there is no use of steam in the process, a very important advantage is the flexibility and improvement of energy efficiency in the process by, instead of steam, using aromatic hydrocarbons formed during the process of converting ethylbenzene to styrene as carrier gas, like benzene or toluene. They have a very high heat capacity and are thermally speaking very stable. More specifically, the heat capacity/heat evaporation ratio for the benzene-toluene mixture is higher than for water-steam, thus resulting in a significantly lower hot utility requirement which will have to be provided by burning additional fuel in a boiler. Although the requirement for cold utility increases, this utility is at much lower costs. The hydrogen gas produced in the process is easy to separate from the rest simply by condensing benzene, toluene, ethylbenzene and styrene out. The condensed product is sent to distillation and benzene, toluene and ethylbenzene are recycled.

Accordingly, the invention is in its broadest aspect a process for the dehydrogenation of alkanes, alkenes or alkylbenzenes to the corresponding unsaturated chemical products and hydrogen ($H_2$) comprising contacting the alkane, alkene or alkylbenzene with a metallic sulfide (MeS) catalyst in which the dehydrogenation is conducted in one or more dehydrogenation reactors without using steam ($H_2O$) as carrier gas for the alkanes, alkenes or alkylbenzenes, and in the presence of hydrogen sulfide ($H_2S$) without formation of $H_2S$ as a reaction product.

Thus, contrary to the prior art the present invention avoids using compounds such as COS which yield $H_2S$ as product in the process. Preferably also, no production of sulfur dioxide ($SO_2$) takes place. Also contrary to the prior art, there is no need to use steam in the process as carrier gas in the dehydrogenation of ethylbenzene to styrene.

The metallic sulfide (MeS) is preferably also provided via a pre-sulfiding step.

As used herein the terms metallic sulfide and metal sulfide are used interchangeably.

As used herein, the term "carrier gas" means a gas which significantly contributes to the dilution of the reactant to favor the thermodynamic equilibrium of the dehydrogenation reaction, suppression of carbon formation on the catalyst and provision of heat of reaction by acting as heat carrier. Accordingly, the carrier gas is a gas that at least represents 20% (mass basis) of the feed to be dehydrogenated such as a feed of alkanes, alkenes or alkylbenzene, or a mixture of these. Several carrier gases may be combined to form the carrier gas, so the carrier gas may then represent at least 90% (mass basis) of the feed to be hydrogenated, preferably at least 100%, more preferably above 200%, i.e. total amount of carrier gas at least 2 times that of the feed to be dehydrogenated.

The term "without using steam ($H_2O$) as carrier gas" means that steam represents below 10% (vol. flow) of the carrier gas used, as it is recognized that small amounts of steam may be carried over or produced in any process stream. For instance, steam may represent 0.5-10% of the carrier gas. More specifically, steam may represent even below 5% of the carrier gas, for instance 1-5% or 0.5-5%. In any case, the major contribution to the dilution of the reactant to favour the thermodynamic equilibrium of the dehydrogenation reaction, suppression of carbon formation on the catalyst and provision of heat of reaction by acting as heat carrier is not provided by steam. In a particular embodiment in connection with the above and below embodiments, the amount of steam in the carrier gas is zero or below detectable limits.

In one particular embodiment in connection with the above or below embodiments, the molar ratio of hydrogen sulfide ($H_2S$) to alkanes, alkenes or alkylbenzene (in the feed) is between 0.01 and 0.2, preferably 0.01-0.1. Hence, small amounts of $H_2S$ are used in the process, particularly at the ppmv level. In one particular embodiment the molar ratio of $H_2S$ to alkanes or alkylbenzene is 0.02-0.05. For instance the concentration of alkanes such as propane can be 10% while $H_2S$ is present in amount 2000 ppmv.

In another embodiment in connection with one of the above or below embodiments, the molar ratio of hydrogen sulfide ($H_2S$) to hydrogen ($H_2$) is between 0.01 and 0.2, preferably between 0.01 and 0.1, more preferably where the temperature of the dehydrogenation process is 600° C. or above. This is the initial molar ratio of $H_2S$ to $H_2$. It has been found that by maintaining $H_2S$ at such proportions, thus resulting in small amounts of $H_2S$ in the process, it is now possible to keep catalyst stability high, as the catalysts are kept as metal sulfides during the dehydrogenation process. Carbon formation, which is the major driver for catalyst deactivation and for concomitant undesired effects such as metal dusting, is thereby suppressed.

The presence of $H_2S$ in the dehydrogenation is maintained by conducting the process in a continuous operation mode. In this manner the catalyst is kept in the sulfided state as MeS. For instance, for Me=Co, the following equilibrium reaction applies:

$$9Co+8H_2S=Co_9S_8+8H_2$$

For which the equilibrium constant can be estimated from $K_p=0.004907*exp(98105/T)$.

The feed to the process in the form of alkanes, alkenes or alkylbenzenes, together with the carrier gas other than steam, is combined with a continuous stream of $H_2S$ which is largely enough to keep the metal, here cobalt in a sulfided state. The skilled person would understand that this amount of $H_2S$ has to be higher than the equilibrium constant $K_p$ at the respective temperature, which is preferably the temperature at the inlet of a dehydrogenation reactor(s). Accordingly, the initial molar ratio of $H_2S$ to $H_2$, e.g. at the inlet of a dehydrogenation reactor(s) will be maintained at about the same low level during dehydrogenation and high enough to keep the metal sulfide (MeS), despite hydrogen being produced during the dehydrogenation.

In a particular embodiment in connection with one of the above or below embodiments, the molar ratio of hydrogen sulfide ($H_2S$) to hydrogen ($H_2$) is 0.05-0.06, for instance 0.055. Again, this is the initial molar ratio of $H_2S$ to $H_2$. We have found surprisingly high conversion and selectivity, particularly for the production of styrene from ethylbenzene, at this specific range. Preferably, the temperature is 600° C. or above, for instance up to 650° C. or 700° C., and the molar ratio of hydrogen sulfide to ethylbenzene is 0.05-0.06, for instance 0.055. Preferably, the catalyst is CoMo oxides supported on a $MgAl_2O_4$ carrier, where the catalyst was sulfidized before use, i.e. pre-sulfidized.

In another embodiment in connection with one of the above or below embodiments, the metal (Me) of the metallic sulfide (MeS) is selected from Fe, Co, Ni, Mn, Cu, Mo, W and combinations thereof. Preferably, the metal is a combination of cobalt (Co) and molybdenum (Mo). Preferably the metal sulfides are supported on alumina or spinels such as magnesium aluminium spinel ($MgAl_2O_4$).

In another embodiment in connection with one of the above or below embodiments, the process is conducted at temperatures in the range 450-700° C., preferably 500-650° C. These temperatures enable the proper conditions for the endothermic dehydrogenation reactions.

The feed to be dehydrogenated consists of alkanes, alkenes, ethylbenzenes and combinations thereof. Preferably the feed is one of alkanes, alkenes or ethylbenzenes.

In another embodiment in connection with one of the above or below embodiments, the alkane is selected from ethane, propane, butane, pentane and combinations thereof.

In another embodiment in connection with one of the above or below embodiments, the alkene is selected from ethylene, propylene, butene, pentene and combinations thereof. The dehydrogenation results in the corresponding unsaturated chemical product, e.g. propadiene/propyn where the alkene in the feed is propylene.

In another embodiment in connection with one of the above or below embodiments, the alkylbenzene is ethylbenzene and the corresponding unsaturated chemical product is styrene.

In another embodiment in connection with one of the above or below embodiments, unreacted alkanes, alkenes, alkylbenzenes and by-products are recycled to the one or more dehydrogenation reactors. The unreacted alkanes and by-products include methane, ethane, ethylbenzene, benzene, toluene, and combinations thereof.

In particular, where the process concerns the dehydrogenation of ethylbenzene to styrene, benzene and toluene are produced in side reactions. Hence, in another embodiment in connection with one of the above or below embodiments, benzene, toluene, or combinations of both, are used as carrier gas. Because of the very high heat capacity of benzene and toluene, as well as their thermal stability, their use as carrier gas in the process instead of steam provides enormous benefits in terms of energy efficiency, i.e. there is a surprisingly drastic reduction in energy consumption in terms of hot utility requirements.

In addition, the side reaction producing benzene also produces ethylene and the side reaction producing toluene also produces methane. Ethane may also be generated as by-product in the process. Hence, in another particular embodiment in connection with one of the above or below embodiments, methane, ethane, or combinations of both, are used as carrier gas. These have also higher heat capacity to heat of evaporation ratios than steam and provide similar benefits in terms of energy efficiency.

Particularly during the production of styrene by dehydrogenation of ethylbenzene, the produced hydrogen gas is easy to separate from the rest of the products (and by-products) by simply condensing benzene, toluene, ethylbenzene and styrene out. Valuable hydrogen can be used as product instead of as diluent as in current conventional dehydrogenation processes, while the condensed product is sent to distillation and benzene, toluene and ethylbenzene are recycled to the dehydrogenation reactors.

In another particular embodiment in connection with one of the above or below embodiments the dehydrogenation is conducted in adiabatic reactors with a reheating step and selective oxidation of hydrogen produced in the process in between the reactors. This embodiment enables even higher energy efficiency. The selective oxidation of the hydrogen produced in the first reactor is preferably conducted over a noble catalyst, such as a Pt-based catalyst.

In yet another particular embodiment in connection with any of the above embodiments, off-gas containing $H_2$ and CH4 produced in the process is used as carrier gas and selective oxidation of hydrogen is conducted upstream the first dehydrogenation reactor. Selective oxidation of hydrogen may thus be conducted upstream the first dehydrogenation reactor and/or upstream the second dehydrogenation reactor. In particular, during the production of styrene from ethylbenzene, the use of benzene-toluene and off-gas containing $H_2$ and $CH_4$ produced in the process as carrier gases, together with the use of selective oxidation of hydrogen upstream the first dehydrogenation reactor and preferably also in between the reactors (e.g. upstream the second dehydrogenation reactor), conveys an even higher energy efficiency. It is not expected to use such a selective oxidation unit upstream the first dehydrogenation reactor, as no hydrogen has been produced as such and accordingly there is no need of such unit, yet by doing so, surprisingly higher energy efficiency is obtained. The person skilled in the art would normally be discouraged to provide a selective oxidation unit upstream the first dehydrogenation reactor. Typical processes using steam as carrier gas would require a steam to ethylbenzene mole ratio of 5-6. The recycled off-gas combined with the air used for the oxidation come on top of this, which means that the recirculation compressor has to compress to significantly higher pressures than in the present invention. In other words, what it would seem to give parasitic high energy consumption turns out in the present invention to give a significant benefit in energy efficiency.

Thus, in a simple and elegant manner, a process is provided in which not only the catalyst remains stable, i.e. no deactivation by coke/carbon formation thereby enabling the catalyst to function for long periods of time without regeneration, but the process is superior to the prior art in terms of energy efficiency, particularly during the production of styrene from ethylbenzene.

The accompanying FIGS. 1-4 serve to illustrate the present invention.

FIG. 1 corresponds to Example 3 and shows a process according to the prior art for conversion of ethylbenzene to styrene, where steam is used as carrier gas.

Figure 2:
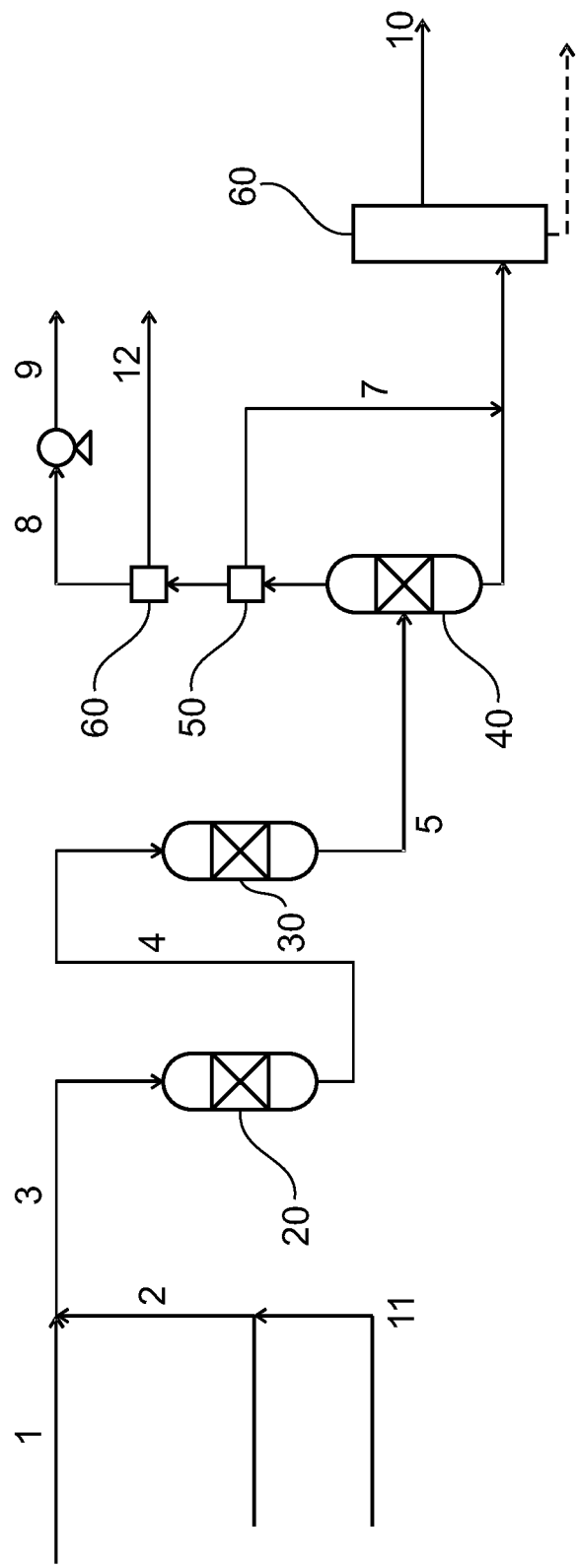

FIG. 2 corresponds to Example 4 and shows a process according to the present invention where ethylbenzene is converted to styrene, in which the carrier gas is a mixture of benzene/toluene and $H_2S$ is also used in the process.

Figure 3:
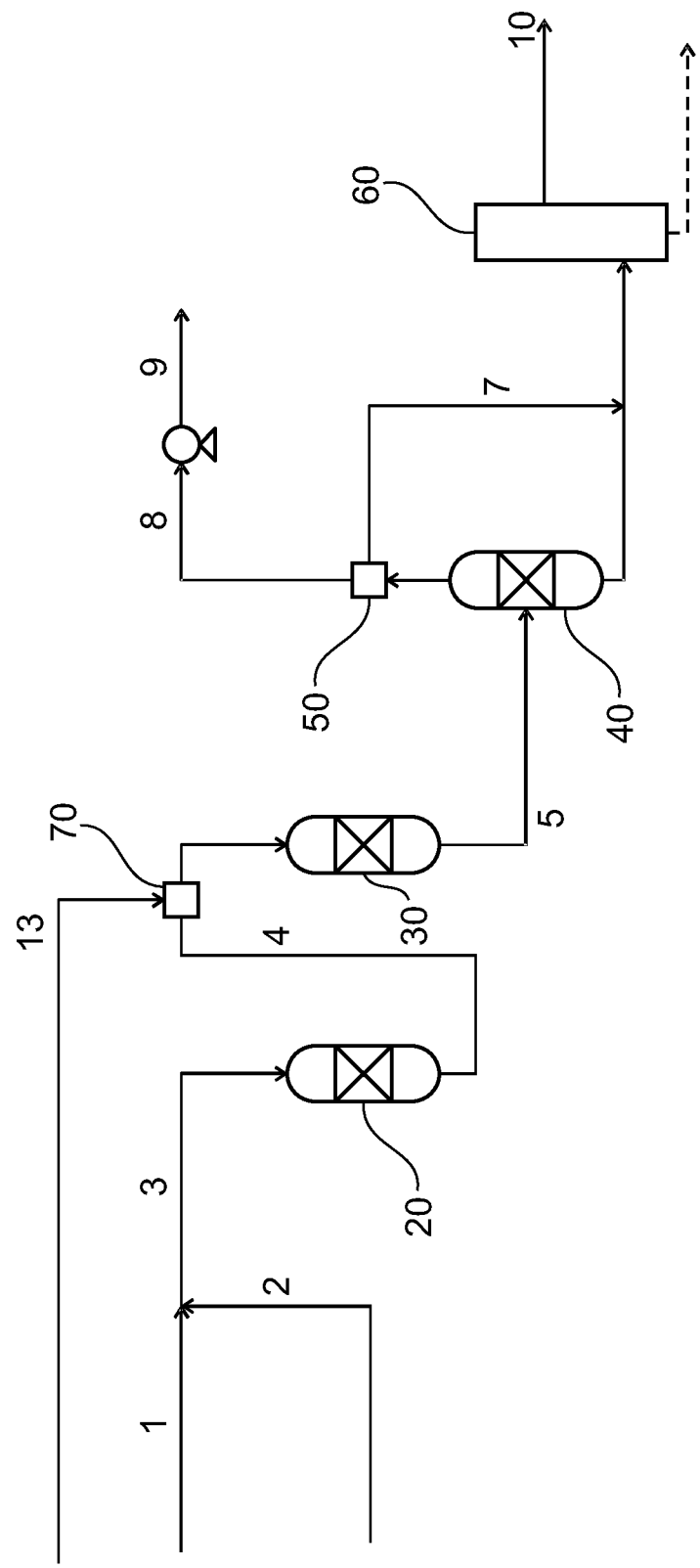

FIG. 3 corresponds to Example 5 and shows a process according to the prior art for conversion of ethylbenzene to styrene, where steam is used as carrier gas, and where selective oxidation of hydrogen produced in the first reactor is conducted.

Figure 4:
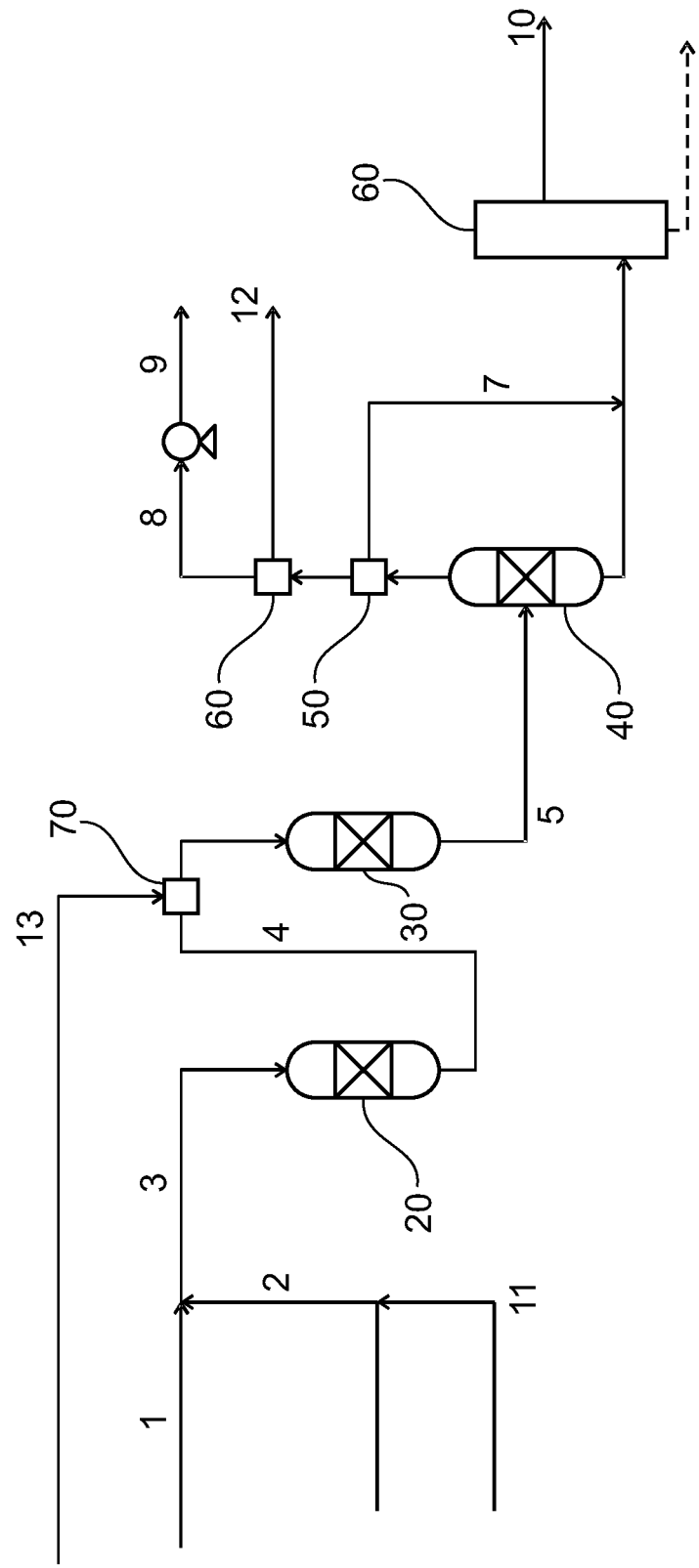

FIG. 4 corresponds to Example 6 and shows a process according to the present invention where ethylbenzene is converted to styrene, in which the carrier gas is a mixture of benzene/toluene, $H_2S$ is also used in the process, and selective oxidation of hydrogen produced in the first reactor is conducted.

Figure 5:
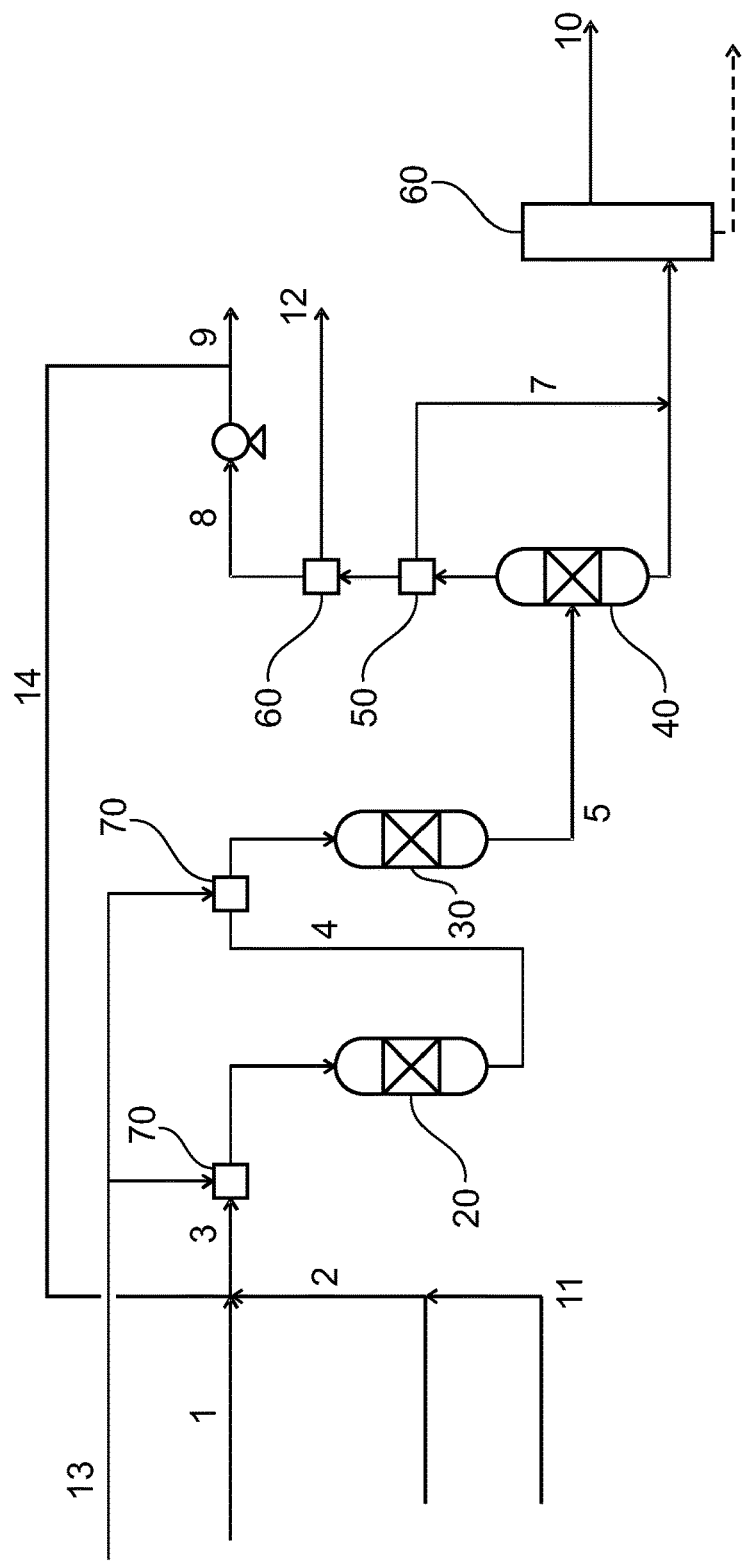

FIG. 5 corresponds to Example 7 and shows a process according to the present invention where ethylbenzene is converted to styrene, in which the carrier gas is a mixture of benzene/toluene and off-gas recycle containing $H_2$ and $CH_4$, $H_2S$ is also used in the process, and selective oxidation before the first and second reactor is conducted.

EXAMPLE 1—INVENTION

Dehydrogenation of Ethylbenzene

The catalyst used consisted of CoMo oxides supported on a $MgAl_2O_4$ carrier the catalyst was sulfidized before use, i.e. presulfidized. The amount loaded in the reactor was 10·g catalyst mixed with 10·g inert material also consisting of $MgAl_2O_4$ (spinel) carrier.

TABLE 1

| Temp. [° C.] | Ethyl benzene [vol %] | Styrene [vol %] | $H_2$ [vol %] | $H_2S$ [vol %] | Styrene conv. [%] | Styrene select. [%] |
|---|---|---|---|---|---|---|
| 550 | 4.39 | 1.81 | 4.64 | 0.31 | 28.8 | 90.9 |
| 550 | 7.42 | 2.19 | 5.01 | 0.31 | 22.5 | 94.8 |
| 550 | 2.97 | 0.88 | 3.71 | 0.31 | 22.8 | 94.2 |
| 575 | 2.61 | 1.10 | 3.92 | 0.31 | 29.1 | 95.2 |
| 575 | 2.47 | 1.00 | 3.82 | 0.31 | 28.4 | 95.2 |
| 575 | 2.54 | 0.94 | 3.77 | 0.31 | 26. | 95.30 |
| 575 | 4.26 | 1.31 | 4.10 | 0.31 | 23.3 | 95.2 |
| 600 | 3.57 | 2.04 | 4.82 | 0.31 | 35.3 | 92.9 |
| 600 | 3.48 | 1.85 | 4.63 | 0.31 | 33.7 | 92.8 |
| 600 | 3.65 | 1.92 | 4.70 | 0.31 | 33.51 | 93.0 |
| 600 | 5.77 | 2.96 | 5.74 | 0.31 | 36.0 | 97.0 |
| 600 | 3.55 | 1.58 | 4.36 | 0.31 | 30.3 | 95.6 |
| 600 | 3.41 | 1.43 | 4.21 | 0.31 | 29.1 | 95.4 |

The loading zone in the reactor was 635 mm to 244 mm from the top flange. The total flow has been around 48 Nl/h throughout the testing period for ethylbenzene dehydrogenation. The pressure was 3 barg, which is the minimum pressure the experiment could be conducted using the present setup. The nonselective products were benzene, toluene, methane, ethane and ethylene. Nitrogen was used as carrier gas. Hydrogen sulfide was added from a hydrogen sulfide/hydrogen mixture thereby adding hydrogen. The surplus of hydrogen may give rise to increased cracking besides limiting the conversion which is relatively close to the calculated equilibrium value.

Only small amounts of $H_2S$ as measured by the molar (vol.) ratio $H_2S/H_2$ are used and in the absence of steam. As shown in Table 1, high styrene conversions (close to equilibrium) and high styrene selectivity are obtained with no carbon formation on the catalyst. Particular high conversion and selectivity are obtained at higher temperatures, which is expected since the reaction is endothermic, yet surprisingly high conversion and selectivity where the $H_2S/H_2$ value is particularly in the range 0.05-0.06, specifically here 0.054 (antepenultimate row of Table 1). The molar ratio of hydrogen sulfide ($H_2S$) to hydrogen ($H_2$) is the initial molar ratio and not after the reaction has been performed.

EXAMPLE 2—INVENTION

Dehydrogenation of Propane

The dehydrogenation of propane was conducted on the same catalyst as the dehydrogenation of ethylbenzene in Example 1. The conditions with respect to pressure and nitrogen as diluent as well as addition of a hydrogen hydrogen sulfide mixture for keeping the catalyst sulfided were the same. The by-products found were methane, ethane and ethylene. No mercaptanes were found. As shown in Table 2 conversions close to equilibrium and high selectivity are obtainable. No carbon formation on the catalyst was detected.

TABLE 2

| Temp. [° C.] | Propene [vol %] | Propane [vol %] | $H_2$ [vol %] | $H_2S$ [vol %] | Propane conversion [%] | Propene selectivity [%] |
|---|---|---|---|---|---|---|
| 550 | 1.41 | 4.14 | 2.20 | 0.24 | 25.2 | 95.3 |
| 575 | 1.43 | 4.19 | 2.20 | 0.24 | 25.0 | 92.1 |
| 550 | 0.56 | 5.60 | 2.20 | 0.24 | 9.00 | 94.1 |
| 550 | 0.46 | 5.74 | 2.20 | 0.24 | 7.38 | 93.6 |

EXAMPLE 3—PRIOR ART

Classic Styrene Process

Styrene is produced in very large quantities worldwide and used in a variety of products. The dominant process today is based on catalytic dehydrogenation of ethylbenzene using an iron based catalyst.

FIG. 1 shows a typical process layout. The figures in this patent application are provided without a detailed heat exchange network, e.g. the streams to be heated and cooled are divided into convenient segments where heating and cooling is carried out to the dew or bubble points in order to provide input to a pinch analysis. The pinch analysis provides answers on what will be the minimum needed hot and cold utility provided a predetermined minimum temperature approach in the heat exchanger network. A minimum approach of 20° C. has been used in all cases (Examples 3-7).

In FIG. 1, ethylbenzene 1 is mixed with steam 2 to form mixed feed stream 3 and preheated to the inlet temperature of 645° C. at the inlet of the first reactor 20. The temperature drops adiabatically to 542° C. across the first reactor due to the reaction. The effluent stream 4 from reactor 20 is reheated to 645° C. before entering the second reactor 30, where effluent 5 leaves at 600° C. It is cooled down to 20° C. before the separator 40, where water is decanted off and the crude styrene/benzene/toluene mixture 6 together with unconverted ethylbenzene is separated out. The remaining traces of aromatics 7 are recovered by means of zeolites or the like in unit 50 and added to the crude styrene stream 6. The off-gas 8 consisting of mainly hydrogen, methane, ethylene and carbon dioxide is compressed to slightly above ambient pressure and used as fuel 9.

The crude styrene stream is sent to the distillation section 60, where styrene product 10 is obtained. A first column (not shown) separates benzene/toluene from ethylbenzene/styrene and a second column (not shown) separates ethylbenzene from styrene. Final purification of the styrene and benzene/toluene separation has not been included in the process comparisons as they are assumed identical in all cases.

The conversion of ethylbenzene to styrene has been fixed to 70% by varying the steam content resulting in a steam to carbon ratio of around 1 or a steam to oil weight ratio of around 1.4 as it is usually expressed in the styrene industry.

The loss of ethylbenzene due to side reactions where ethylbenzene is respectively converted to benzene, ethylene and to toluene, methane is calculated by transforming 2% of the styrene into ethylene and benzene and 3% into toluene and methane.

All the calculations have been made with a production of 100 MT per hour of styrene leaving the ethylbenzene/styrene splitter column of the second distillation column.

The result of the pinch analysis of the process is shown in Table 3. The hot utility is 307 MW (Relative hot utility=100).

EXAMPLE 4—INVENTION

New Styrene Process

In this example, the other two functions of steam, namely dilution of reaction mixture and heat carrier, are performed by recycling a benzene/toluene mixture, i.e. a benzene/toluene mixture is used as carrier gas. This stream can be obtained by recycle from the product separation columns, i.e. the first distillation column.

The process is illustrated by FIG. 2.

Recycled benzene/toluene stream 2 is added instead of steam to fresh and recycled ethylbenzene 1 together with enough $H_2S$ in stream 11 to keep the catalyst sulfide throughout the reactor train according to the equilibrium

$$9Co+8H_2S=Co_9S_8+8H_2$$

For which the equilibrium constant can be estimated from $K_p=0.004907*\exp(98105/T)$.

The feed to the first reactor comprises therefore ethylbenzene, a small amount of $H_2S$ and benzene/toluene as carrier gas. Hydrogen sulfide is recuperated as stream 12 after the benzene/toluene recovery 50.

The result of the pinch analysis in Table 3 shows that the hot utility requirement is only 278 MW or about 9% lower than the process of Example 4 (prior art).

EXAMPLE 5—PRIOR ART

Improved Classic Styrene Process

In an improved version of the classic process (Example 3, FIG. 1) the reheat between the two reactors is provided by selective oxidation in unit 70 using air 13 over a noble metal catalyst of part of the hydrogen produced in the first reactor. FIG. 3 illustrates this concept. The result of the pinch analysis (Table 3) show that this process configuration reduces the need for hot utility to 263 MW which is a substantial improvement compared to the classic process of Example 3 (14% better energy efficiency, from 100 to 86 in terms of relative hot utility), especially because the medium used for reheat between the two reactors in Example 3 is steam superheated to very high temperature, as high as 890° C., which however also requires expensive high alloy steels for construction.

EXAMPLE 6—INVENTION

New Styrene Process with Selective Hydrogen Oxidation

In this embodiment the selective hydrogen oxidation 70 using air 13 in between dehydrogenation reactors is combined with the recycle of benzene/toluene as carrier gas 2 and the addition of small amounts of $H_2S$ in stream 11 according to the invention. This is illustrated in FIG. 4. The result of the pinch analysis in Table 3 shows a surprisingly higher effect on energy efficiency giving rise to about 23% percentage points improvement (from 278 MW to 214 MW of hot utility). The expected result would have been a 14% improvement, as for the prior art processes as described in Example 5.

EXAMPLE 7—INVENTION

New Styrene Process with Selective Hydrogen Oxidation Before Both Reactors

Even better energy efficiency is achieved by introducing also an off-gas recycle back to the first reactor. The principle is illustrated in FIG. 5. The off-gas recycle 14 consisting mainly of $H_2$, $CH_4$ and $N_2$ is also serving as diluent and heat carrier but a small amount of benzene/toluene 2 is also used. Selective oxidation unit 70 is also added upstream the first reactor 20. The result from the pinch analysis in Table 3 shows that the need for hot utility is decreased all the way down to 186 MW and 29% below that of the improved prior art process of Example 5 (263 MW of hot utility). The need for compression energy increases from 1 to 8.5 MW, yet the benefits in energy efficiency are still surprisingly high.

The results of the calculations are summarized in Table 3:

TABLE 3

| Process | Hot Utility, MW | Cold Utility, MW | Relative Hot Utility |
|---|---|---|---|
| Ex. 3 - Prior art | 307 | 145 | 100 |
| Ex. 4 - Invention | 278 | 238 | 91 |
| Ex. 5 - Prior art | 263 | 167 | 86 |
| Ex. 6 - Invention | 214 | 197 | 70 |
| Ex. 7 - Invention | 186 | 203 | 61 |

The benefits of the inventive process using a sulfur passivated dehydrogenation catalyst are i.a.:

A) The need for hot utility, which will have to be provided by burning additional fuel in a boiler, is significantly lower when avoiding the use of steam as carrier gas but using a benzene/toluene mixture instead.

B) Where off-gas recycle and selective hydrogen oxidation is introduced (Ex. 7) the need for hot utility is reduced even more significantly and it is almost 40% (Ex. 3) or 29% below that of the prior art processes, Ex. 3 and Ex. 5 respectively.

The invention claimed is:

1. A process for the dehydrogenation of alkanes, alkenes and/or alkylbenzenes to the corresponding unsaturated chemical products and hydrogen ($H_2$), comprising:
    contacting a carrier gas comprising (1) one of benzene and a benzene-toluene mixture, and (2) alkane, alkene and/or alkylbenzene compounds to be dehydrogenated with a pre-sulfided metallic sulfide (MeS) catalyst, in which the dehydrogenation is conducted in one or more dehydrogenation reactors in the presence of $H_2S$ without formation of $H_2S$ as a reaction product, wherein the carrier gas further comprises: (1) 0.5% to less than 10% by volume steam ($H_2O$), (2) hydrogen sulfide ($H_2S$) at a molar ratio of $H_2S$ to the alkane, alkene and/or alkylbenzene compounds to be dehydrogenated between 0.1 and 0.2, and (3) an initial molar ratio of hydrogen sulfide to hydrogen ($H_2$) between 0.01 and 0.2, wherein said alkane, alkene and/or alkylbenzene compounds comprise at least one of: (1) ethylbenzene, and (2) methane, ethane, or a combination thereof; and recovering a product stream comprising unsaturated chemical products.

2. The process according to claim 1 in which the initial molar ratio of hydrogen sulfide ($H_2S$) to hydrogen ($H_2$) is 0.05-0.06.

3. The process according to claim 1, in which Me of the metallic sulfide (MeS) catalyst is selected from Fe, Co, Ni, Mn, Cu, Mo, W and combinations thereof.

4. The process according to claim 1, in which the process is conducted at temperatures in a range of 500-700° C.

5. The process according to claim 1, wherein the alkylbenzene compound is ethylbenzene, and styrene is the unsaturated chemical product.

6. The process according to claim 1, in which unreacted alkanes, alkenes, alkylbenzenes and by-products in the product stream are recycled to the one or more dehydrogenation reactors.

7. The process according to claim 6, in which the unreacted alkanes, alkenes, alkylbenzenes and by-products in the product stream include methane, ethane, ethylbenzenes, benzene, toluene, and combinations thereof.

8. The process according to claim 1, wherein said carrier gas further comprises methane, ethane, or combinations of both.

9. The process according to claim 1, wherein the one or more dehydrogenation reactors are adiabatic reactors with a reheating step and selective oxidation of hydrogen produced in the process between the adiabatic reactors.

10. The process according to claim 1, in which off-gas containing $H_2$ and $CH_4$ produced in the process is used as a part of the carrier gas and selective oxidation of hydrogen is conducted upstream of a first dehydrogenation reactor.

* * * * *